July 16, 1940. J. ROSENBERG Plant Pat. 412

TOBACCO PLANT

Filed Oct. 14, 1936 2 Sheets-Sheet 1

INVENTOR.
JOSEPH ROSENBERG
BY Toulmin & Toulmin
ATTORNEYS

July 16, 1940. J. ROSENBERG Plant Pat. 412

TOBACCO PLANT

Filed Oct. 14, 1936 2 Sheets-Sheet 2

INVENTOR.
JOSEPH ROSENBERG

BY Faulmann & Faulmann
ATTORNEYS

Patented July 16, 1940

Plant Pat. 412

UNITED STATES PATENT OFFICE

412

TOBACCO PLANT

Joseph Rosenberg, Hartford, Conn., assignor to The Rosenberg-Coulter Corporation, Hartford, Conn., a corporation of Connecticut Application October 14, 1936, Serial No. 105,603

1 Claim. (Cl. 47—59)

My invention relates to a new type of tobacco plant and to improvements therein.

My invention consists of a tobacco plant that is propagated optionally by cuttings or by seed. It is further characterized by the fact that it has a single stalk without supplementary or branch stalks at the top.

My invention is characterized by leaves, the stem of which at the base adjacent to the stalk for an appreciable distance has substantially no leaf structure; the leaf itself is ovate in shape, having a broad base and a relatively broad body tapering to a sharp point. The vein structure of the leaf is so arranged that in practically all leaves for the first third to two-thirds of the distance to the base of the leaf towards the tip, the oppositely disposed veins branch from the longitudinal vein substantially from opposite positions.

My invention is further characterized by the fact that the leaf is extremely thin in texture throughout its entire structure from base to tip and practically all of the leaves are of this same thin texture. The top leaves are not thick and full of starch as in the customary tobacco leaf.

My tobacco grows very thin in texture from top to bottom, due to the closeness of the leaves, which shades the leaves from the strong sun rays, and when the top leaves are exposed to the sun without any protection by other leaves, the leaves remain thin, due to the fact that the food moving from the root is distributed evenly by the great number of leaves and no great amount of food is allowed to settle in the top of the plant to cause the leaves to thicken.

My invention is further characterized by the fact that the root structure is formed from a plurality of relatively heavy, laterally extending, tuber members from which the fine roots depend. Very little if any of the root structure extends directly downwardly from the base of the stalk, but practically all of the heavy root structure extends laterally and peripherally from the bottom of the stalk.

My tobacco is characterized by the fact that it grows in such states as Connecticut without the use of shade, which is characteristic of tobacco grown in that State. It produces an average of from 35 to 40 leaves per stalk instead of from 15 to 20 leaves that are available for picking on a shade tobacco plant.

My invention is further characterized by the fact that there is a single stem with no sucker leaves.

My invention is further characterized by the fact that more marketable leaves are produced by my new variety of tobacco plant than the tobacco plants heretofore grown in the northern part of the United States.

My invention is characterized by a lack of sucker leaves.

Referring to the drawings:

Figure 5 illustrates an oblique cross-section taken through the plant stock and illustrates the number of leaf stems extending out from the stock along a 360 degree spiral line around the stock.

Figure 1:
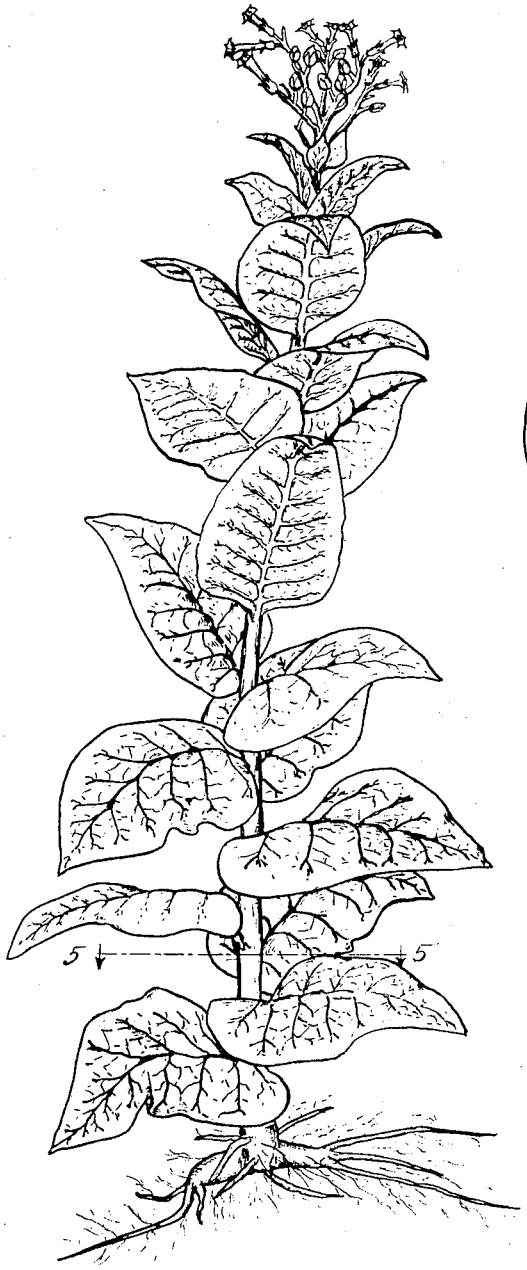
Figure 1 is a side elevation of the plant showing the single stalk, the arrangement of the leaves and the root structure. Some of the leaves have been omitted for the purpose of clarity in the drawings.
Figure 2:
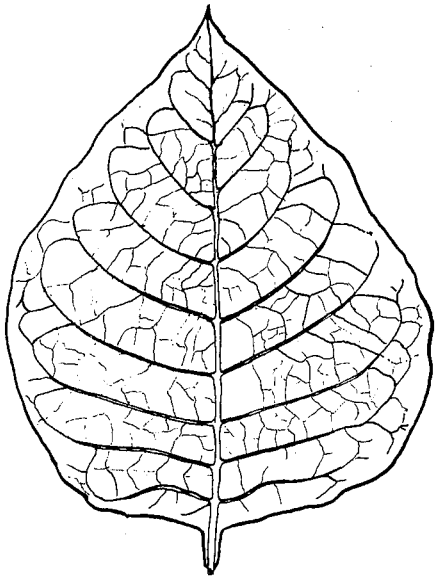
Figure 2 is a plan view of one of the leaves showing the arrangement of the vein structure.
Figure 5:
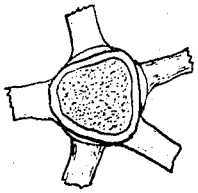
Figure 5 is a section on the line 5—5 of Figure 1.

This plant contains a maximum of about 40 leaves, of which 35 are usable. It reaches a height of about seven feet. It does not grow any suckers on the stalk. The blossom is not topped, as is customary with most other tobacco, as the root grows in a more compact mass and extends much deeper. Therefore, the object in topping tobacco, which is to ripen it and with Connecticut shade tobacco to spread the root to avoid the tobacco falling over from the weight of the rain or wind, is eliminated.

Another characteristic of my invention in this tobacco plant is that it never becomes spotted, no matter how ripe it becomes. Its color is uniform and it does not make any difference when you pick it after it has reached its full growth. The vein system in my plant is such that the food is distributed evenly through the cells and consequently my tobacco does not show dead cell spots, which are yellow in color and make the leaf spotted, greatly decreasing the value of wrapper tobacco.

It is characterized by the fact that it can be grown from cuttings. After the plants grow to a suitable point, they can be slipped and these cuttings will take root in about one week and grow the same type of plants as from the original plant.

The greatest damage to all tobacco, whose value is in its color as wrapper, occurs from the inability of the veins to evacuate the waste matter in the process of curing. This is far more destructive than any growing conditions. The distribution of the plant food is effected by the veins. If the canals in the veins become partly closed, the food and water cannot get out through their usual channels and the result is discoloration in the form of stained leaf, stems and white veins. None of this condition occurs with my tobacco due to the fact that the veins surrounding the nest are round and do not break down, and therefore there is no discoloration in any form. My tobacco is cured without the necessity of barn fires, as much be used by all shade growers to cure their tobacco. My tobacco has free flow of waste matter.

The tobacco of my invention has an improved burning superior to any other type of wrapper tobacco. It does not have to be fertilized to improve the burn, as in the case of all other types of wrapper tobacco. It is a neutral tasting tobacco, both in the tongue taste and smoke taste.

The leaves grow with a very thin texture, with a symmetrical vein structure, due to the number of leaves which grow close together. This close growing leaf structure protects the leaves from the strong sun rays and the tobacco leaves do not become thickened due to the even distribution of the plant food.

Heretofore tobacco became thick and dark from the middle of the plant upwardly due to the fact that the food was forced to the top of the plant and the sun converted the food into starch, which made the leaves thick. Due to the fact that the plant of my invention has such a large number of leaves and uniformly distributed vein structure, there are so many more outlets for the plant food en route from the stalk that the food is more evenly distributed and some of the leaves are not overfed and consequently do not get unusually thick, which renders the leaves useless for wrappers for cigars.

No claim is made as to novelty in color.

Figure 3:
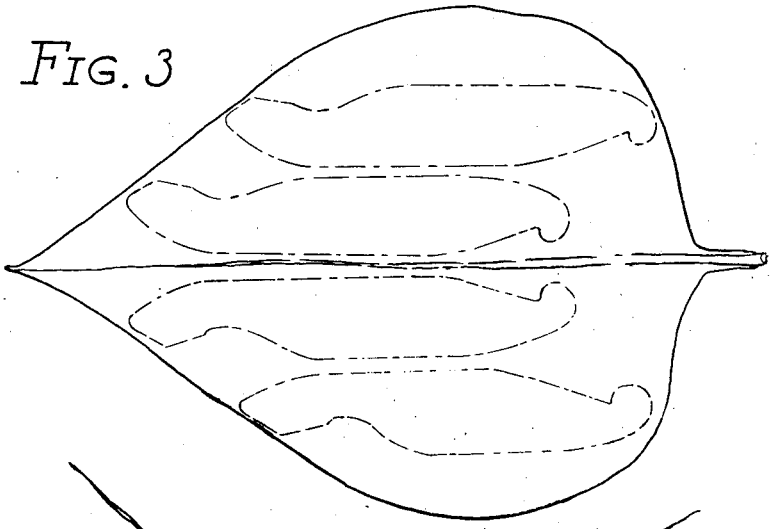
Figure 3 is a diagrammatic view of the leaf showing the outline of the dies used for cutting the wrappers for cigars from this leaf to illustrate the advantage of the broad base leaf.
Figure 4:
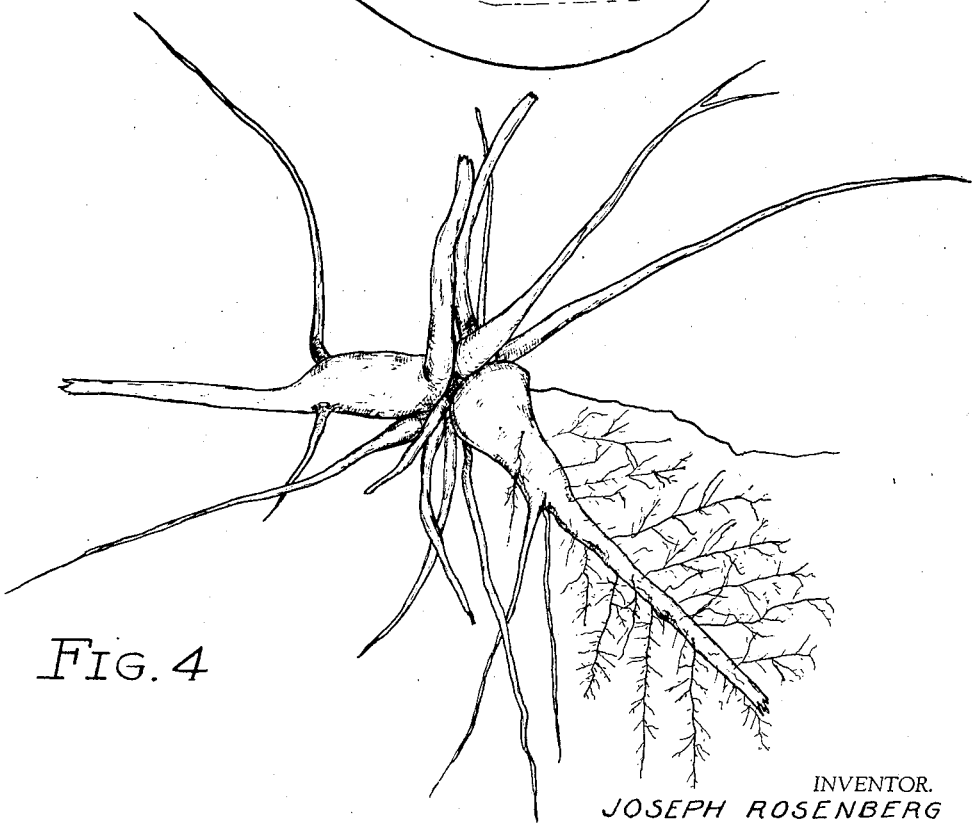
Figure 4 is a bottom plan view of the root structure with the minor roots removed except on one of the major roots. This illustrates a heavy, tuber-like root structure on the base of the stalk or stem, said root structure extending substantially horizontally and laterally about the periphery of the base of the stem.

In Figure 3 the diagrammatic leaf form is shown with the outlines on either side of the central stem structure of a pattern of the shape of the wrapper that is put on the cigars by machinery. The end marked "head" is taken from the lower end of the leaf, which in this leaf of my invention has the extreme amount of spread. The other end of this die which is marked "tuck" is taken from the tip end of the leaf. This wrapper die is reversible as indicated to provide a right and left wrapper.

It is obvious that with this form of leaf it is possible to secure very much better wrappers and a larger quantity thereof from a given leaf.

It is to be understood that the foregoing characteristics are typical but subject perhaps to slight variation which may arise by reason of change of environment.

I claim:

An asexually reproducible variety of tobacco plant, adapted to be grown unaided by shade means, characterized by a single stalk having leaves of wide ovate shape and of relatively thin, flat uniform texture; all the leaves on said plant being substantially of the same thickness and having an appreciable stem at the base of the leaf structure with substantially no leaf structure or fringe on the stem at the base of the leaves, and having a root structure at the base of the stalk of heavy tuber character which extends substantially radially about the periphery of the stalk at the base of the plant.

JOSEPH ROSENBERG.